(12) United States Patent
Koda

(10) Patent No.: US 6,699,178 B1
(45) Date of Patent: Mar. 2, 2004

(54) ENDOSCOPIC AUDITORY CANAL CLEANING APPARATUS

(75) Inventor: Yoshiharu Koda, Tokyo (JP)

(73) Assignee: Coden Co. Ltd., Tokyo (JP)

( * ) Notice: Subject to any disclaimer, the term of this patent is extended or adjusted under 35 U.S.C. 154(b) by 144 days.

(21) Appl. No.: 09/713,723

(22) Filed: Nov. 15, 2000

(30) Foreign Application Priority Data

Nov. 15, 1999 (JP) .......................................... 11-323590
Jul. 18, 2000 (JP) ...................................... 2000-217978

(51) Int. Cl.⁷ ................................................. A61B 1/00
(52) U.S. Cl. ..................................... 600/104; 600/101
(58) Field of Search ................................. 600/199, 200, 600/127, 129, 104, 101; 606/161, 162

(56) References Cited

U.S. PATENT DOCUMENTS

| | | | | | |
|---|---|---|---|---|---|
| 3,638,643 | A | * | 2/1972 | Hotchkiss | ....................... 128/9 |
| 4,411,265 | A | * | 10/1983 | Eichenlaub | ............... 128/303.1 |
| 4,572,180 | A | * | 2/1986 | Deenadayalu | ............... 128/304 |
| 5,060,632 | A | * | 10/1991 | Hibino et al. | ................... 128/6 |
| 5,209,757 | A | * | 5/1993 | Krug et al. | .................. 606/162 |
| 5,325,847 | A | * | 7/1994 | Matsuno | ........................ 128/4 |
| 5,762,605 | A | | 6/1998 | Cane et al. | |
| 5,888,199 | A | * | 3/1999 | Karell et al. | ................. 606/162 |
| 5,916,150 | A | * | 6/1999 | Sillman | ........................ 600/184 |
| 5,938,590 | A | * | 8/1999 | Elliott | ........................ 600/184 |
| 5,944,711 | A | * | 8/1999 | Pender | ........................ 604/514 |
| 5,961,441 | A | | 10/1999 | Plumb et al. | |
| 6,059,719 | A | * | 5/2000 | Yamamoto et al. | ......... 600/127 |
| 6,093,155 | A | * | 7/2000 | Ouchi | ........................ 600/569 |
| 6,155,987 | A | * | 12/2000 | Scherl | ........................ 600/562 |
| 6,168,604 | B1 | * | 1/2001 | Cano | ........................... 606/114 |
| 6,500,114 | B1 | * | 12/2002 | Petitto et al. | ................ 600/156 |

FOREIGN PATENT DOCUMENTS

| | | |
|---|---|---|
| JP | U-2-132494 | 11/1990 |
| JP | A-6-269474 | 9/1994 |
| JP | A-8-173382 | 7/1996 |
| WO | WO 97/33530 | 9/1997 |

* cited by examiner

*Primary Examiner*—Henry Bennett
*Assistant Examiner*—Nihir Patel
(74) *Attorney, Agent, or Firm*—Woodbridge & Associates; Richard C. Woodbridge; Roy Rosser

(57) ABSTRACT

The invention intends to provide an ear-pick, which is capable of safely and securely remove earwax, and foreign objects such as insects and water.

Endoscopic auditory canal cleaning apparatus comprising: an ear-pick main body, which is equipped with a scraping part at its distal end and is formed to guide light to said distal end; a light source, which generates said light; a light source generates light; a fiber scope, which captures images in the inside of the auditory canal; a display unit, which displays the images captured by the fiber scope; and a holding part, which holds the ear-pick main body and the fiber scope; wherein the fiber scope passes through a hollow opening provided in the holding part; and the holding part holds the fiber scope to be able to rotate freely.

8 Claims, 16 Drawing Sheets

ENDOSCOPIC AUDITORY CANAL CLEANING APPARATUS

BACKGROUND OF THE INVENTION

1. Field of the Invention

The invention relates to an ear-pick, which is capable of removing earwax safely and securely.

2. Description of the Prior Art

A conventional ear-pick is basically a stick with a small spoon-like portion or a cotton blob at its end. Therefore, if one wished to remove ear wax or foreign objects such as an insect or water in one's ear, the only thing one could do was to scratch the inside of the ear blindly with an ear-pick because one could not see the inside of the auditory canal.

However, there is the danger of hurting the inside of the ear in scratching the inside of one's ear blindly so that it is hardly a safe thing to do. Thus, it has been very difficult to clean the inside of one' own ear by oneself using the conventional ear-pick.

SUMMARY OF THE INVENTION

The present invention intends to provide an ear-pick that enables one to remove earwax and foreign objects such as insects or water from the inside of one's ear safely and securely.

The invention is an endoscopic auditory canal cleaning apparatus comprising: an ear-pick main body having a scraping part at its distal end, to which light is being introduced; a light source that generates said light; an image capturing means that captures images of the inside of the ear canal; a display means that displays the images captured by the image capturing means; and a holding part that holds the ear-pick main body; wherein the image capturing means passes through a hollow opening provided in the holding part and the holding part rotates freely around the image capturing means.

In the present invention, the light from the light source radiates the inside of the auditory canal via the ear-pick main body. The images of the inside of the auditory canal, which is illuminated by the light, are captured by the image capturing means and guided to the display means, which displays them. The user can remove foreign objects while watching their images. Moreover, since the holding part can rotate around the image capturing means, the holding part and the ear-pick main body can be rotated together to clean the inside of the auditory canal while the images displayed by the display means are held in a fixed direction.

DETAILED DESCRIPTIONS OF THE INVENTION

Several embodiments of the invention will be described in detail in the following referring to the accompanying drawings.

Embodiment 1

Figure 1:
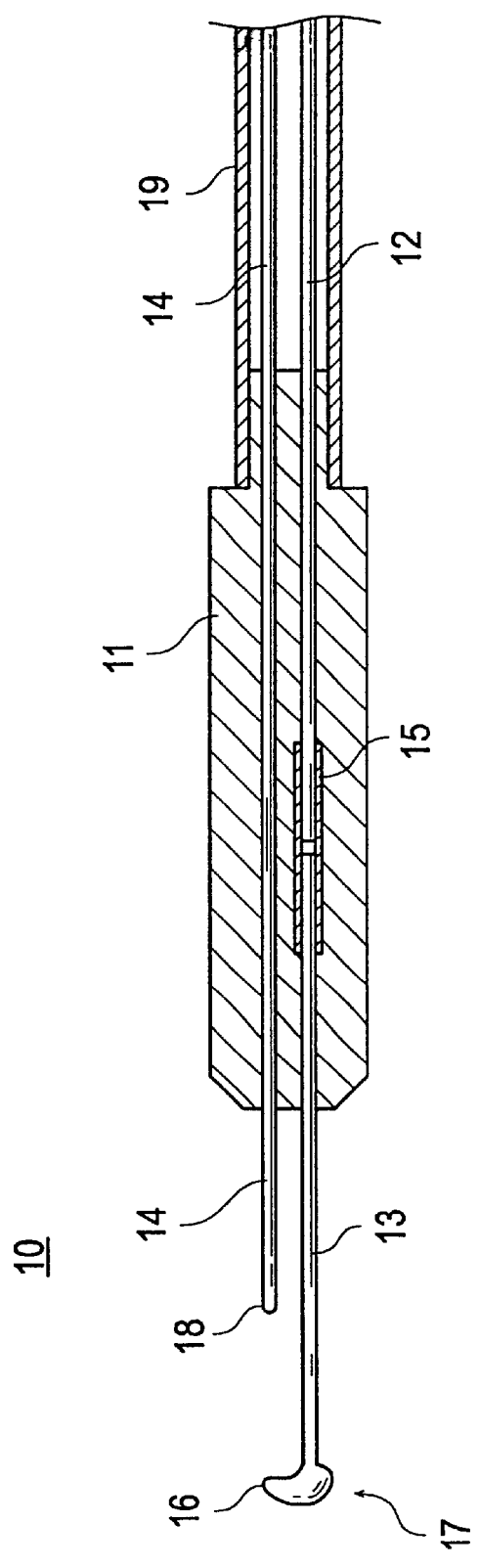
FIG. 1 is a cross section of the ear-pick unit of an endoscopic auditory canal cleaning apparatus.

FIG. 1 is a cross section of the ear-pick unit 10 of an endoscopic auditory canal cleaning apparatus according to the invention.

The endoscopic auditory canal cleaning apparatus is equipped with a display device that consists of an image display devise and a light source, relays the light from the light source to the holding part (holder) of the ear-pick via an optical fiber, and irradiates this light into the auditory canal from the irradiating part of the ear-pick main body. It also captures the images of the inside of the auditory canal by means of the fiber scope, and displays the images on the display device. Therefore, a person can very easily clean the auditory canal by oneself.

A stick-like holding part 11 holds an optical fiber 12, which is a light guiding means for guiding the light, a ear-pick main body 13 made of a clear plastic for guiding the light receives (relays) the light from the optical fiber 12 and guides the light into the auditory canal, and a fiber scope (image guide) 14 for guiding the images in the auditory canal to the outside. The optical fiber 12 and the ear-pick main body 13 are jointed and fastened together by means of a light guide jointing part 15 and pass through the holding part 11. The distal end (the end that is inserted into the auditory canal) of the ear-pick main body 13 is provided with an earwax removing part (scraping part) 16 for removing earwax and an irradiating part 17 that irradiates the inside of the auditory canal.

The fiber scope 14 has a light receiving part 18 for capturing the images of the inside of the auditory canal and passes through the holding part 11. The light receiving part 18 of the fiber scope 14 has an object lens. This object lens can be provided not only on the distal end of the fiber scope 14 but also in the vicinity or on the side of the distal end. A prism can be used in place of the object lens as well.

As shown in FIG. 1, the ear-pick main body 13 is protruding from the holding part 11 toward the direction of insertion into the auditory canal. The optical fiber 12 is located in the direction opposite to the ear-pick main body 13 from the holding part 11. The fiber scope 14 is protruding both in the direction toward the auditory canal and in the opposite direction. The amount of protrusion of the fiber scope 14 in the direction of insertion into the auditory canal is slightly longer than a half of the protrusion amount of the ear-pick main body 13 considering the easiness of capturing the images in the vicinity of the earwax removing part 16.

The amount of protrusion of the fiber scope 14, however, can be either larger or smaller than a half of the protrusion of the ear-pick main body 13 as long as it does not interfere with the earwax removing action of the earwax removing part 16 and it does not interfere with capturing the images in the auditory canal. The amount of protrusion of the fiber scope 14 also varies with the focal distance of the object lens provided on said fiber scope 14. The parts of the optical fiber 12 and the fiber scope 14 protruding in the direction opposite to the ear-pick main body 13 are both protected by the lead protection tube 19 in order to prevent the optical fiber 12 and the fiber scope 14 from being bent, and are connected to the display device (not shown).

Since the ear-pick main body 13 can be easily contaminated and damaged, it is so designed that it can be inserted or removed for the replacement purpose at the light guide jointing part 15 from the side that the earwax removing part 16 is provided.

Figure 2:
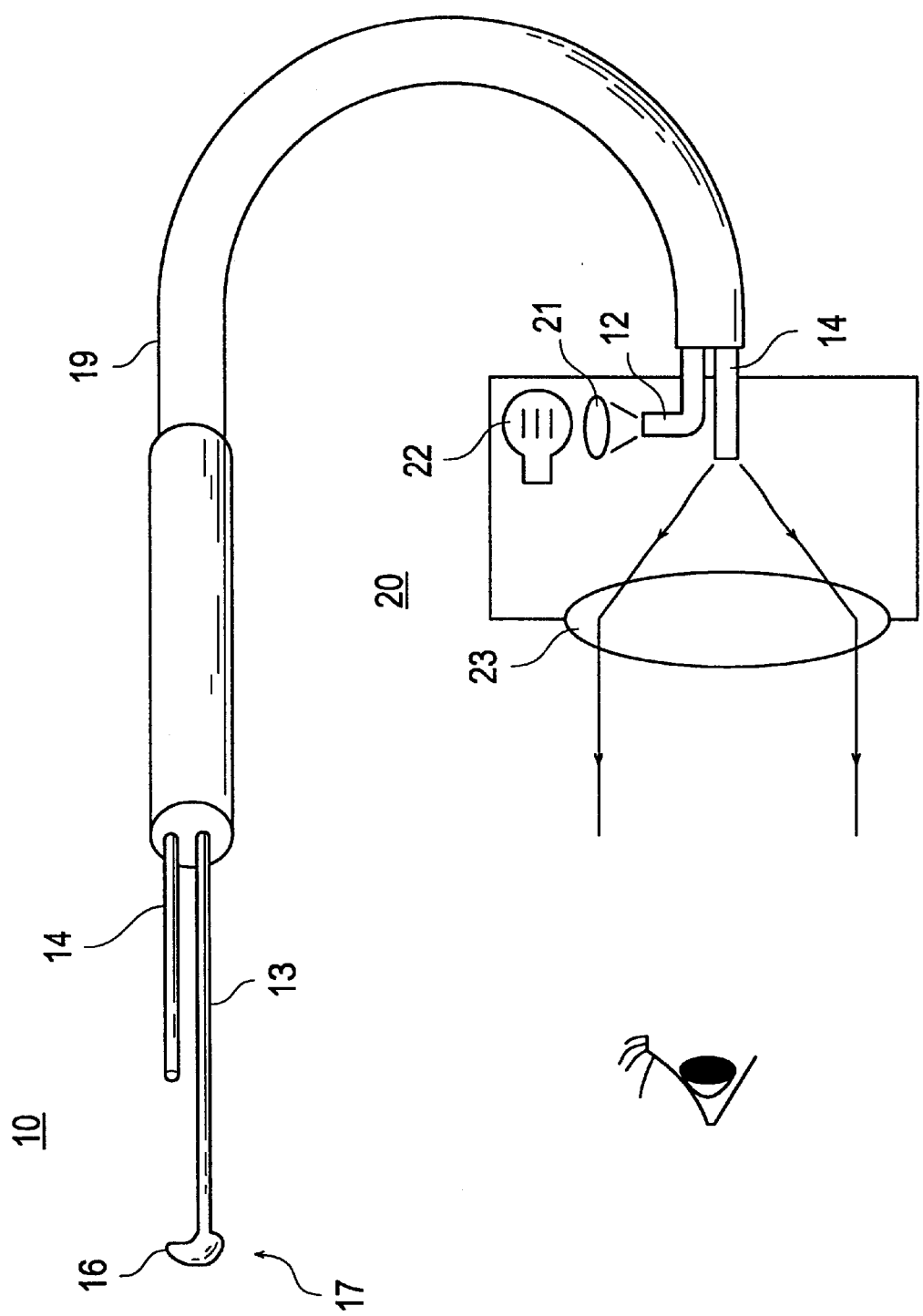
FIG. 2 is a drawing showing the ear-pick unit and a display device.

FIG. 2 is a drawing showing the ear-pick unit 10 shown in FIG. 1 and a display device 20. As described above, the optical fiber 12 and the fiber scope 14 are inserted into the lead protection tube 19 that is connected to the ear-pick unit 10.

The proximal end face of the optical fiber 12 is placed close to the focal position of a condenser lens 21 in the display device 20. The condenser lens 21 collects the light from a light source 22 and irradiates the light to the proximate end of the optical fiber 12. The light is then guided to the ear-pick main body 13 via the optical fiber 12 and radiates from an irradiating part 17.

The proximal end face of the fiber scope 14, i.e., the end of the display device 20 side, is placed at the focal position of the display lens 23. The images inside the auditory canal are captured through the light receiving part 18, transmitted through the fiber scope 14, and displayed through the display lens 23. The display lens 23 can be replaced by a CCD camera, etc. If a CCD camera, etc., is used, the images transmitted through the fiber scope 14 are received by the CCD camera, etc., signal processed, and are displayed on a liquid crystal display or CRT.

Figure 3:
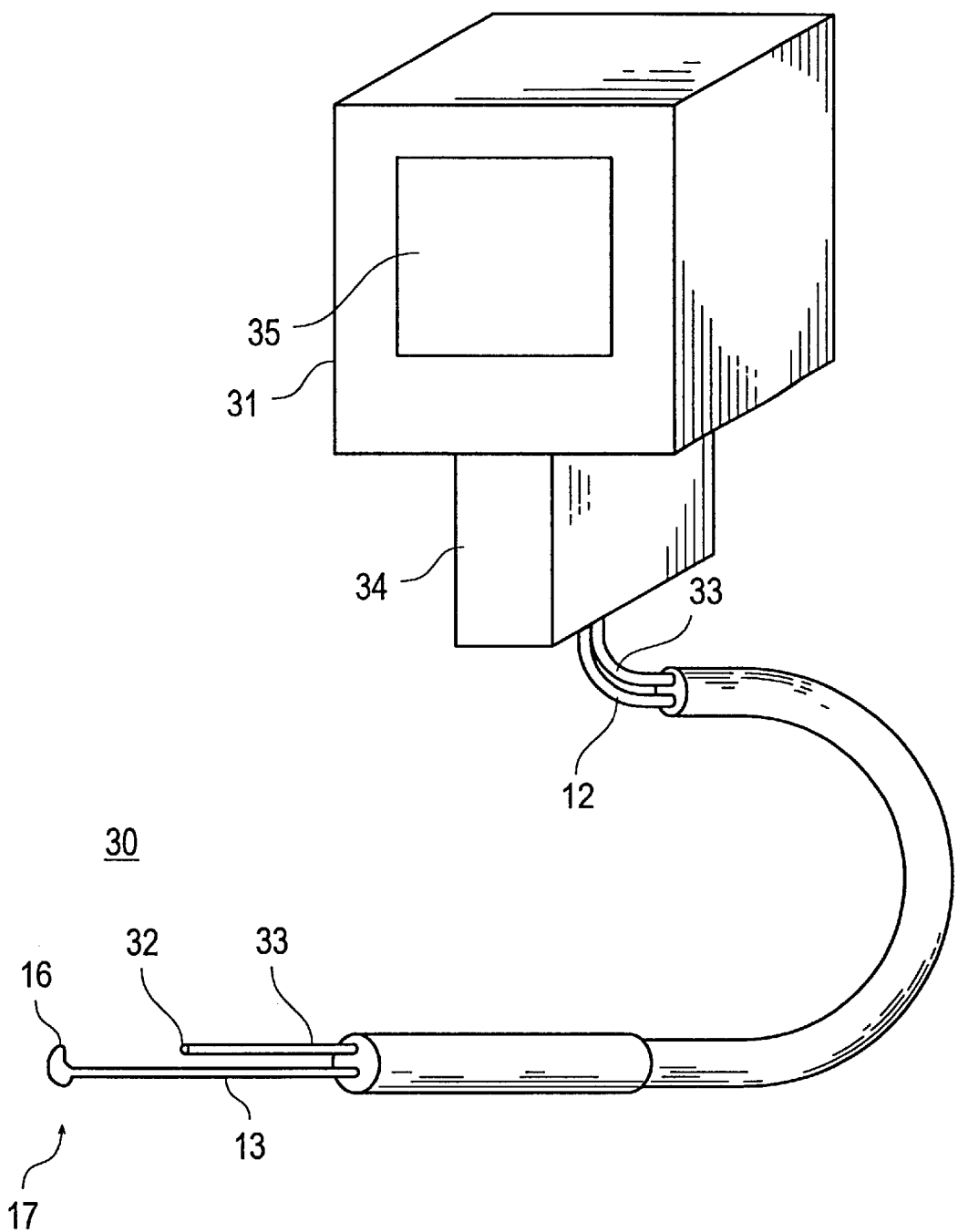
FIG. 3 is a drawing showing the ear-pick unit and the display device when a CCD is used as an image guide.

FIG. 3 is a drawing showing a ear-pick unit 30 and a display device 31 when a CCD is used as the image guide.

The ear-pick unit 30 is the same as the ear-pick unit 10 shown in FIG. 1 except that a CCD camera 32 is used instead of the fiber scope 12 as the light receiving part 18 of the ear-pick unit 10. The members that are assigned with the same numbers as in FIG. 1 function the same way as in the case of FIG. 1 so that their descriptions are not repeated here.

The ear-pick unit 30 has the CCD camera 32 as a means of capturing the images of the inside of the auditory canal. When the inside of the auditory canal is illuminated by the irradiating part 17, the CCD camera 32 captures the images inside the auditory canal. The images captured by the CCD camera are transmitted to a display device 31 by a lead wire 33. The transmitted signals are processed by an image processing device provided in a handle 34 of the display device 31 and are displayed as images at an image display unit 35. The handle 34 contains a light source to provide light to the irradiating part 17.

The CCD camera can be mounted not only on the distal end of the image guide, but also in the vicinity of or on the side of the distal end.

Although it was described in the first embodiment that the light source is placed in the display device, the invention should not be construed to be limited to that. The light source can be placed in the holding part to illuminate the ear-pick main body directly.

Embodiment 2

Figure 4:
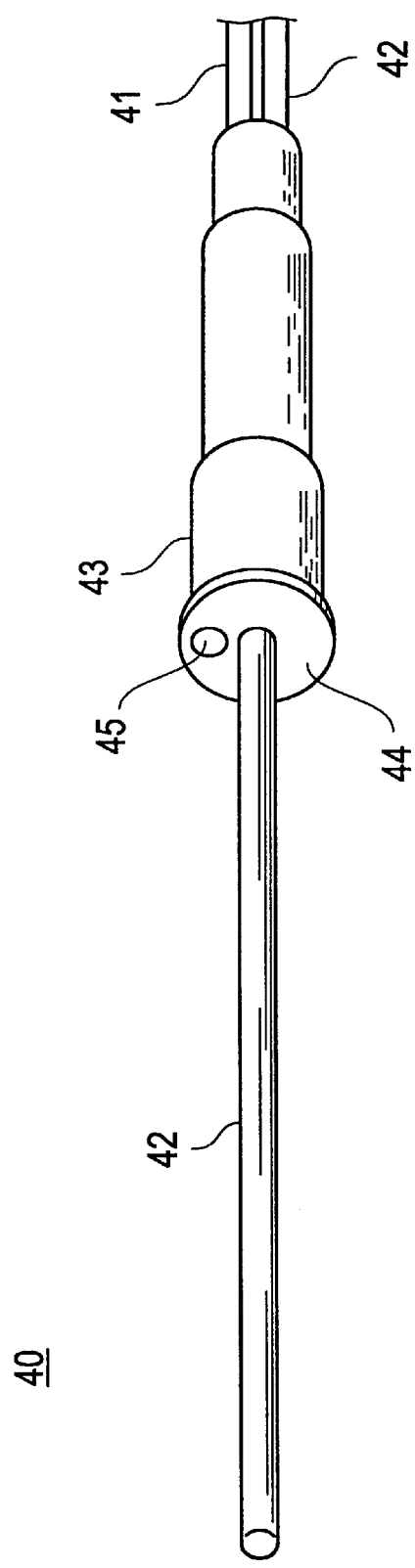
FIG. 4 is a drawing showing a joint holding part of the ear-pick unit.
Figure 5:
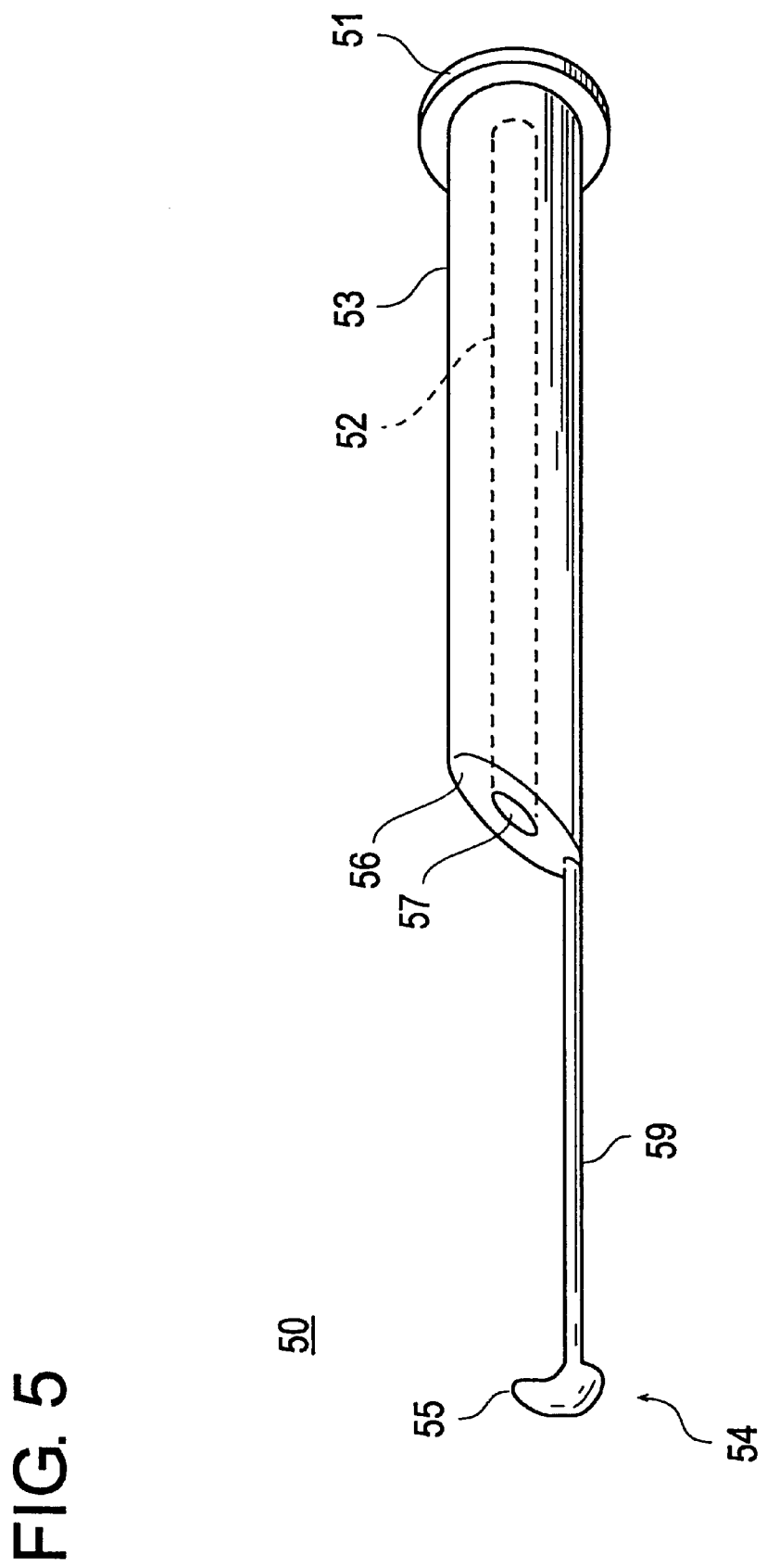
FIG. 5 is a drawing showing a ear-pick main body.
Figure 6:
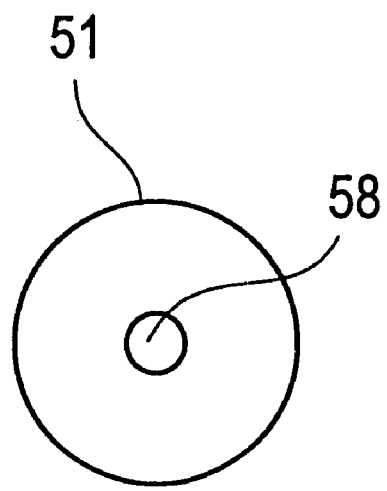
FIG. 6 is a drawing showing a light receiving face of the ear-pick main body.

The second preferred embodiment of the invention will be described below referring to FIG. 4, FIG. 5 and FIG. 6. FIG. 4 is a drawing showing a joint holding part 40 of an endoscopic auditory canal cleaning apparatus of the second embodiment. FIG. 5 is a drawing showing an ear-pick main body 50 of the endoscopic auditory canal cleaning apparatus of the second embodiment. FIG. 6 is a drawing showing a light receiving face 51 of the ear-pick main body 50.

The joint holding part 40 contains an optical fiber 41 that transmits light from a light source of an external display device (not shown) and a fiber scope (image guide) 42 that transmits images of the inside of the auditory canal and holds them by means of its holding part 43. The end face 44 of the holding part 43 is formed with an irradiating face 45 for irradiating the light from the optical fiber 41. A cylindrical fiber scope 42 is protruding at the center of the end face 44. The fiber scope 42 passes through a through-opening 52 of the ear-pick main body 50 shown in FIG. 5. The distal end of the fiber scope 42 is provided with an objective lens. However, the objective lens can be provided not only at the distal end of the fiber scope 42, but also in the vicinity of or on the side of the distal end. A prism can be used in place of the object lens as well.

The ear-pick main body 50 is made of a material with an excellent light transmission capability such as clear plastic and contains as a unit the ear-pick barrel 53 provided with the through-opening 52 for allowing the fiber scope 42 to pass through, an irradiating part 54 for irradiating the auditory canal 54 and a earwax removing part (scraping part) 55 for removing earwax. The ear-pick barrel 53 is formed with a light receiving face 51, which receives light from the irradiating face 45 by abutting the end face 44 of the joint holding part 40 and which also has an inlet of the through-opening 52, and a slanted face 56, which has an outlet 57 of the through-opening 52, on the other side. A light transmission passage 59 extends from the lower position of the slanted face 56 and has the irradiating part 54 and the earwax removing part 55 formed on its distal end.

Figure 7:
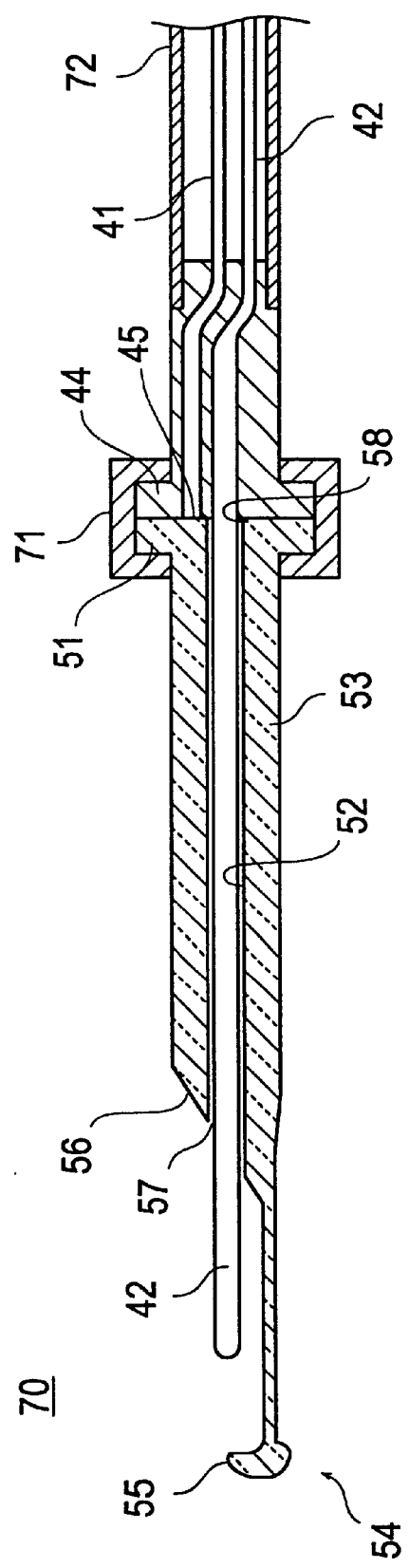
FIG. 7 is a cross section of the ear-pick unit that consists of the joint holding part and the ear-pick main body.

FIG. 7 is a cross section of an ear-pick unit 70 that consists of the joint holding part 40 and the ear-pick main body 50.

The joint holding part 40 and the ear-pick main body 50 are held together rotatably by means of a keeper 71 such as a ring contacting with the irradiating face 44 and the light receiving face 51 together. The keeper 71 can be freely engaged or disengaged. The ear-pick main body 50 is rotatable around the fiber scope 42. Since the ear-pick main body 50 is rotatable, the direction of the earwax removing part 55 can be changed arbitrarily despite the fact that the joint holding part 40 is affixed by the lead protection tube 72. Moreover, since the keeper can be removed freely, the ear-pick main body 50 is also replaceable.

The optical fiber 41 and fiber scope 42 of the joint holding part 40 pass through a lead protection tube 72 and are connected to a display device (not shown). The optical fiber 41 guides light from a light source in the display device, and emits the light at the irradiation face 44. The light emitted from the irradiation face 44 is received by the light receiving face 51, transmitted to the rod-like light transmission pass 59 via the ear-pick barrel 53 and its slanted face 56, and radiated from the irradiating part 54. The images of the inside of the auditory canal irradiated by the irradiating part 54 are captured by the fiber scope 42. The captured images are transmitted to the display device via the fiber scope 42.

The constitution of the display device is identical to the description of FIG. 2 so that it is not repeated here.

Although the fiber scope 42 is used as the image guide in the second embodiment, a CCD can be used as the image guide as well. In this case, the CCD camera and the lead wire at the distal end must be joined together to form a slender rod-like shape at least in the area where they protrude from the joint holding part. The method of joining them together can be inserting them together in a pipe or forming them together with a plastic material.

The display device using a CCD as the image guide is the same as the display device described in relation to FIG. 3.

The CCD camera can be provided not only at the distal end of the image guide, but also in the vicinity of or on the side of the distal end.

Although it was described in the second embodiment that the light source is placed in the display device, the invention should not be construed to be limited to that. The light source can be placed in the holding part to illuminate the ear-pick main body directly.

Embodiment 3

The endoscopic auditory canal cleaning apparatus of the third preferred embodiment of the invention has a light source that illuminates the ear-pick main body directly.

Figure 8:
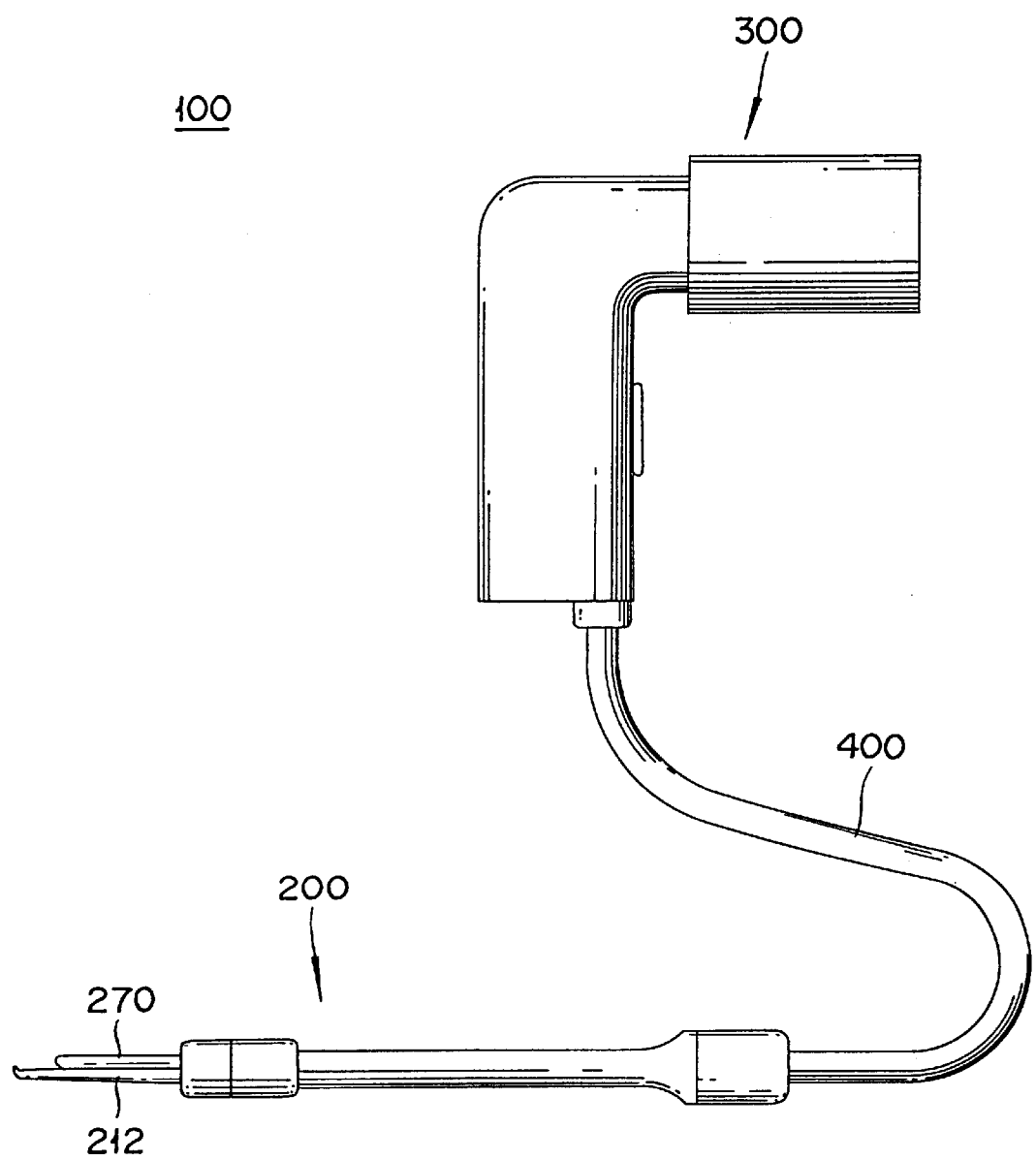
FIG. 8 is a whole view of an endoscopic auditory canal cleaning apparatus according to a third embodiment.

FIG. 8 is a whole view of the endoscopic auditory canal cleaning apparatus 100 of the third preferred embodiment of the invention.

The endoscopic auditory canal cleaning apparatus 100 consists of a ear-pick unit 200 and a display device 300. The ear-pick unit 200 comprises an ear-pick main body 212 and an image capturing means 270. The ear-pick main body 212 provides for illumination and cleaning of the inside of the auditory canal. The image capturing means 270 provides capturing of the images of the inside of the auditory canal. The captured images are transmitted via an image guide (fiber scope) inserted into a protective tube 400, which connects the ear-pick unit 200 and the display device 300, and are displayed on the display device 300.

Figure 9:
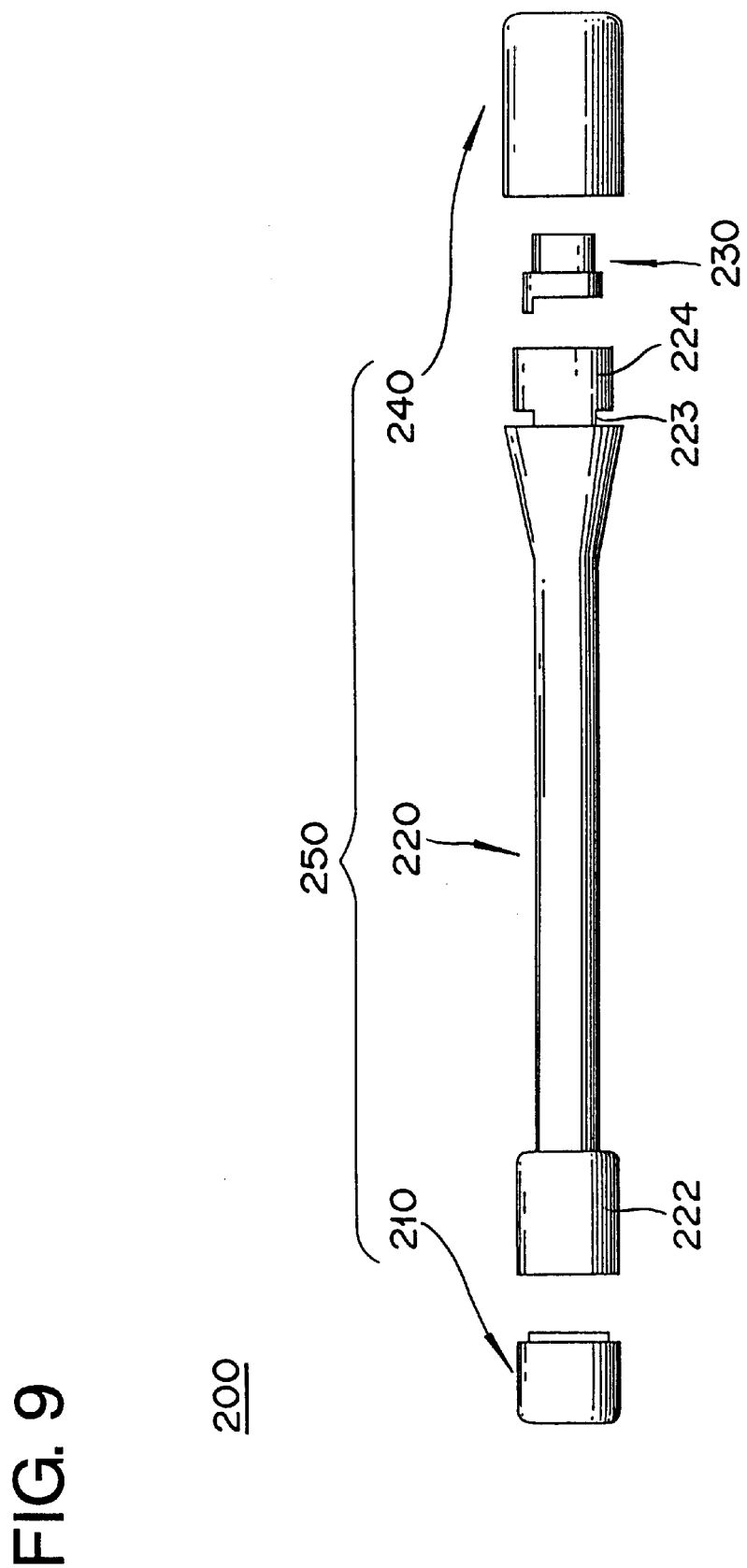
FIG. 9 is a drawing showing the constitution of the ear-pick unit.

FIG. 9 is a drawing showing the constitution of the ear-pick unit 200.

The ear-pick unit 200 comprises an ear-pick mounting part 210, a holding pipe 220, an image guide fixing part 230, and a jointing part 240. The ear-pick mounting part 210 is joined together with the first end 222 of the holding pipe 220 by means of ultrasonic welding or a screw means. The second end 224 of the holding pipe 220 has a notch 223 and is joined together with the jointing part 240 as a result of a hook formed on the inner face of the jointing part 240 engaging with said notch 223. The inside of the second end 224 is set with an image guide fixing part 230 leaving a slight space between them. The holding pipe 220 is freely rotatable around the image guide fixing part 230.

The ear-pick mounting part 210, the holding pipe 220 and the jointing part 240 are joined together linearly to form a holding part 250. The ear-pick mounting part 210, the holding pipe 220 and the jointing part 240 are all formed in hollow shapes. A hollow space is formed in the holding part 250, which is formed by joining these hollow members together, as described later.

The constitution of the ear-pick unit 200 will be described below in detail.

Figure 10:
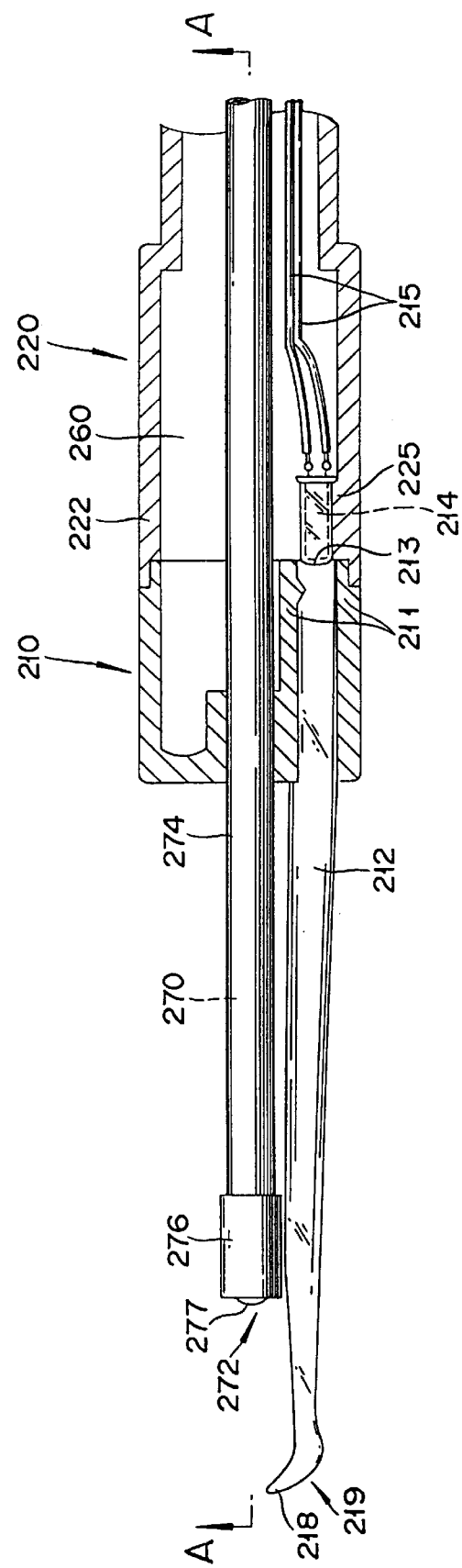
FIG. 10 is a cross section showing how an ear-pick mounting unit and a first end of a holding pipe are connected.
Figure 11:
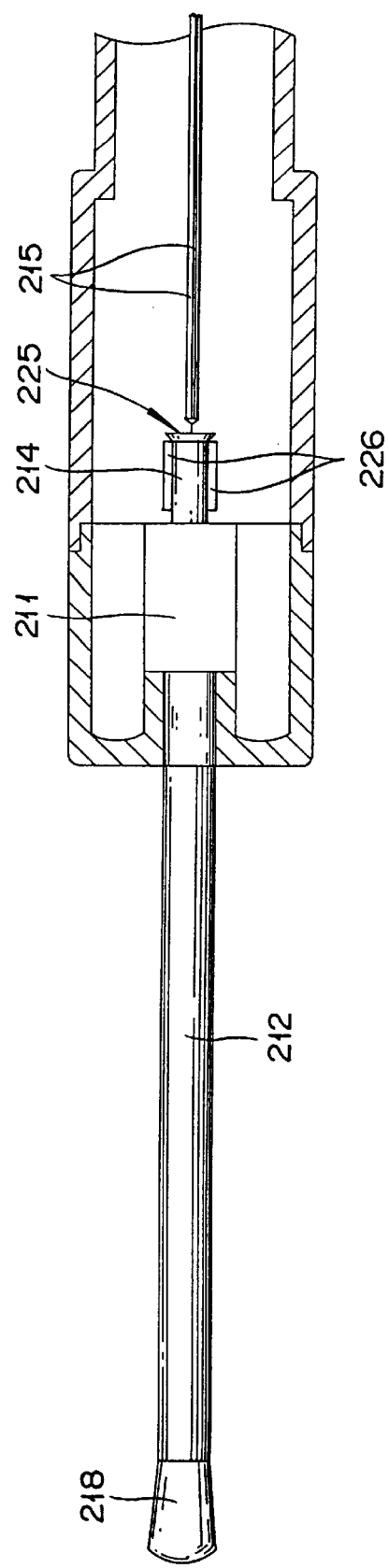
FIG. 11 is a cross section along the A—A line of FIG. 10.
Figure 12:
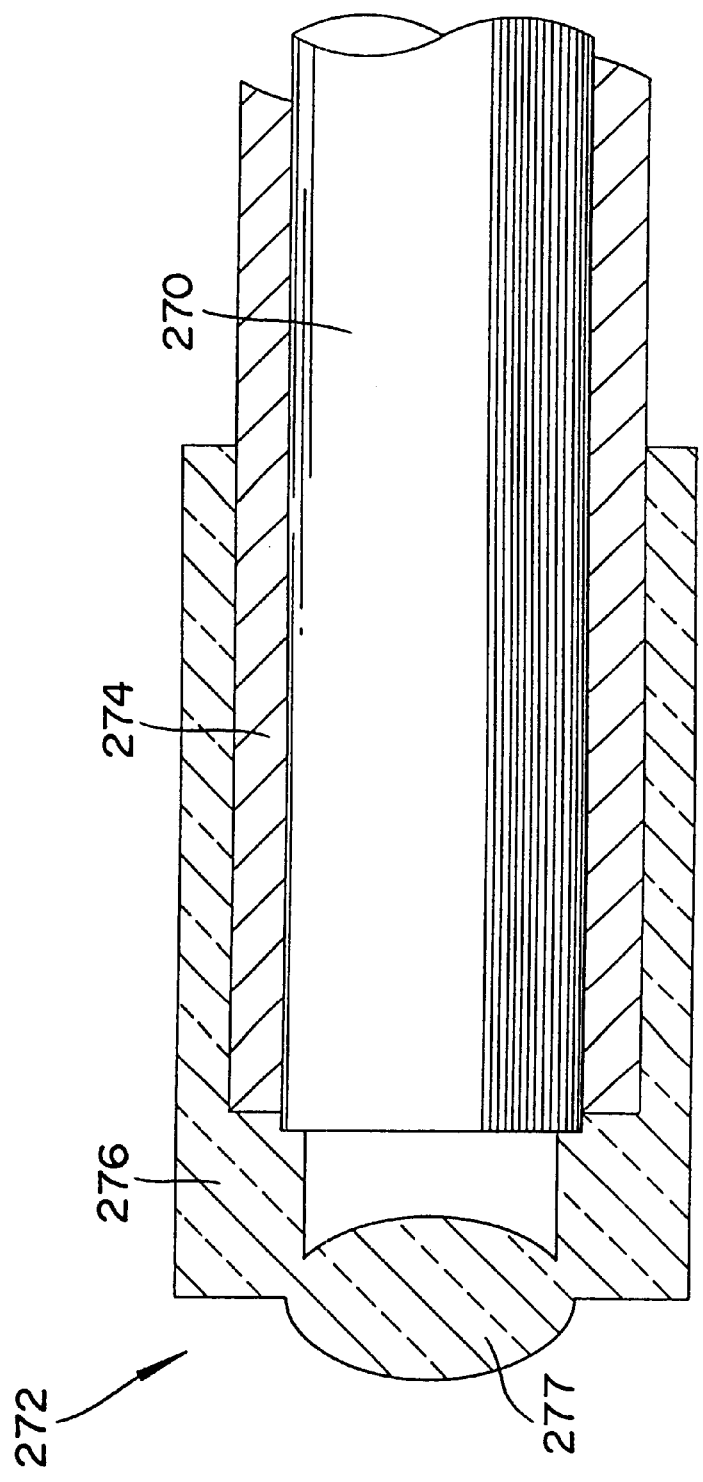
FIG. 12 is a cross section of the cover.

FIG. 10 is a cross section showing how the ear-pick mounting part 210 and the first end 222 of the holding pipe 220 are joined, FIG. 11 is a cross section along the line A—A of FIG. 10, and FIG. 12 is a cross section of a cover 276. The image capturing is not shown in FIG. 11 for the sake of clarity of the drawing.

The ear-pick mounting part 210 is formed in a hollow shape and is attached to the first end 222 of the hollow holding pipe 220. The ear-pick mounting part 210 and the supporting pipe 220 form together a portion of an inner space 260. The inner space 260 is provided with a fiber scope 270, which is the image capturing means, and a light source 214, which generates the light that illuminates the auditory canal.

The fiber scope 270 has a light receiving part 272 to capture the images of the inside of the auditory canal. The fiber scope 270 is held in a straight line, except the distal end, being covered by a protective pipe 274 made of stainless steel to prevent it from breakage or bending as shown in FIG. 12. The fiber scope 270, being held in a straight line, passes through the holding part 250. The distal end of the fiber scope 270 is covered by a replaceable cover 276 that prevents soiling, contamination, and damage of the light receiving part 272 in order to prevent the deterioration of its sight.

The cover 276 is formed with an objective lens 277 into one piece. Therefore, when the object lens 277 is clouded due to the repeated use of the auditory canal cleaning apparatus 100, the objective lens 277 can be replaced easily by replacing the cover 276. In other words, there is no need for mounting the objective lens independently on the distal end of the fiber scope 270 and it is quite simple to replace the clouded lens. It is preferable to unitize the objective lens 277 with the cover 276 to be in the vicinity of or the side of the fiber scope 270 where the cover 276 is mounted on. A prism can be used in lieu of the objective lens 277. Although FIG. 12 shows a case where the cover 276 and the objective lens 277 are formed in one piece using the same material, it is also possible to form the cover 276 and the objective lens 277 with different materials as independent objects or an unitized object.

Moreover, it is also possible to install the objective lens in the inside of the distal end of the protective pipe 274 made of stainless steel, and joint the fiber scope with the lens. In this case, a transparent cover is installed to prevent the contamination of the lens. Thus, the contamination and damage of the image capturing means is prevented.

The light source 214 can be, for example, a light emitting diode (LED) and a incandescent lamp. The light source 214 is placed on a base 225 formed on the inner wall of the supporting pipe 220 as shown in FIG. 10. Moreover, the light source 214 is supported by a pair of wall members 226 formed on both sides of the base 225 as shown in FIG. 11. The light source 214 positioned by means of the base 225 and the wall members 226 is facing an end face 213 of the ear-pick main body 212. The light source 214 receives electric power from a display device 300 via two lead wires 215 and irradiates the end face 213. The light source 214 irradiates the end face 213 of the ear-pick main body 212 directly so that it is capable of supplying the light to the ear-pick main body 212 without any attenuation of its intensity.

The ear-pick main body 212 receives light from the light source 214 at the end face 213 and transmits the received light into the auditory canal. The ear-pick main body 212 is formed of clear plastics for the sake of transmitting light. The clear plastics used here include cycloolefin polymer, acrylic resin, polycarbonate, vinyl chloride resin, styrene resin, APO resin, and polymethacrylate. It is preferable to use cycloolefin polymer as the material for the ear-pick main body 212 because of its low hygroscopicity and excellent light transmitting characteristic and heat resistance. It is also possible to provide a convex lens between the light source 214 and the ear-pick main body 212 to collect light from the light source 214 and supply it to the ear-pick main body 212.

An earwax removing (scraping) part 218 for removing earwax and a irradiating part 219 that illuminates the auditory canal are provided at the distal end of the ear-pick main body 212. The light is irradiated from the irradiating part 219 to illuminate the auditory canal. The earwax removing part 218 is provided where it can be observed from the light receiving part 219 of the fiber scope 270. However, the earwax removing part 218 is provided at the location where it does not obstruct more than a half of the field of view of the fibers cope 270. Since the earwax removing part 218 does not obstruct the field of view of the fiber scope 270, the observation of the auditory canal and the safe cleaning of the auditory canal can be accomplished. It is preferable that the earwax removing part 218 is bent toward the center axis of the fiber scope. It is also preferable that the length of the fiber scope 270 that protrudes from the ear-pick mounting part 210 is more than a half of the length of the ear-pick main body 212 that protrudes from the ear-pick mounting part 210 considering the easiness of capturing the images in the vicinity of the earwax removing part 218. It is further preferable that the distal end of the fiber scope 270 is located 10 mm to 15 mm away from the earwax removing part 212. However, as long as it does not inconvenience the image capturing in the auditory canal and the removal of foreign objects in the auditory canal by the earwax removing part 218, the protruding length of the fiber scope 270 can be either longer or shorter than a half of the protruding length of the ear-pick main body 212.

The ear-pick main body 212 engages with a pair of engaging members 211 provided in the inside of the ear-pick mounting part 210, being free to engage or disengage by means of a male-female fit. Since the ear-pick main body 212 is interchangeable, it is possible to change the size of the ear-pick main body 212 to the one that has an earwax removing part 218 of different size depending on whether it is used for adults or children. It is also hygienically advantageous to be able to replace the ear-pick main body when it gets contaminated and damaged.

Figure 13:
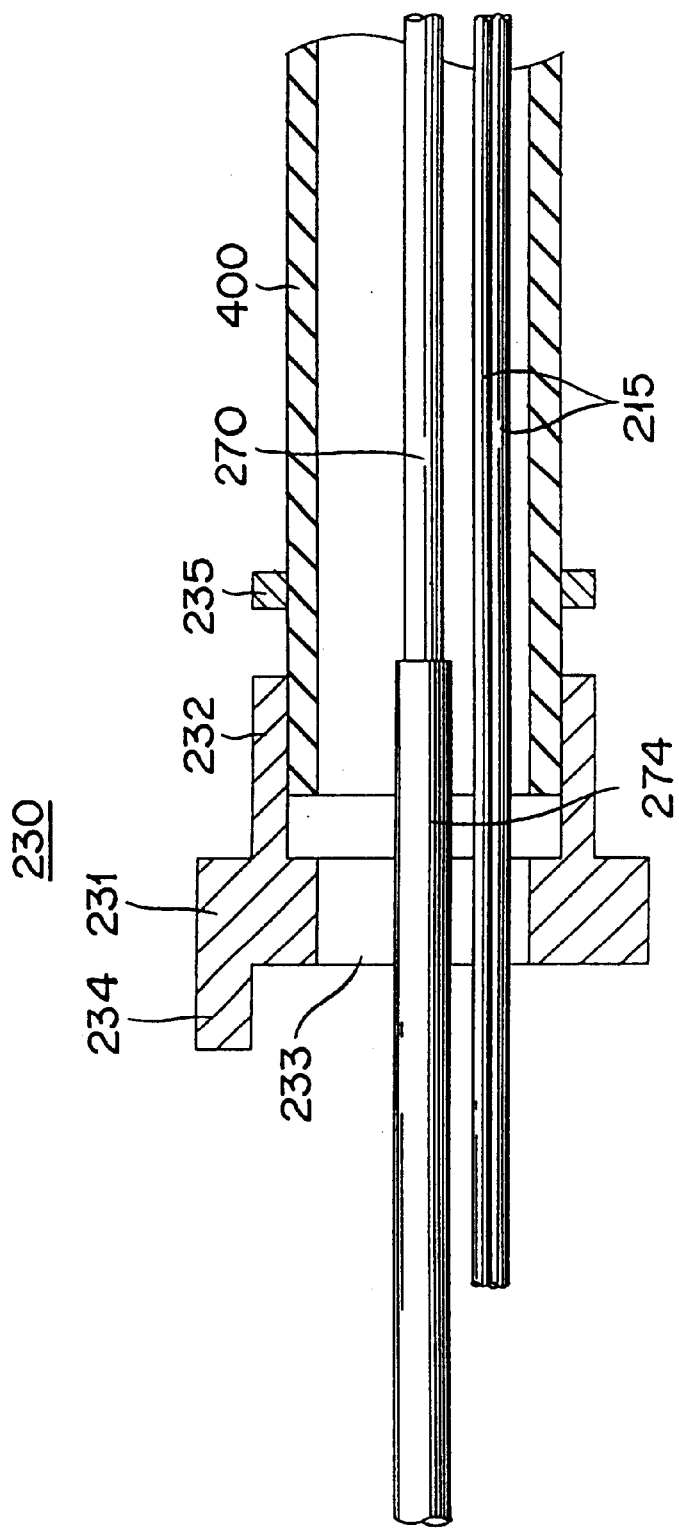
FIG. 13 is a cross section of the image guide fixing part.
Figure 14:
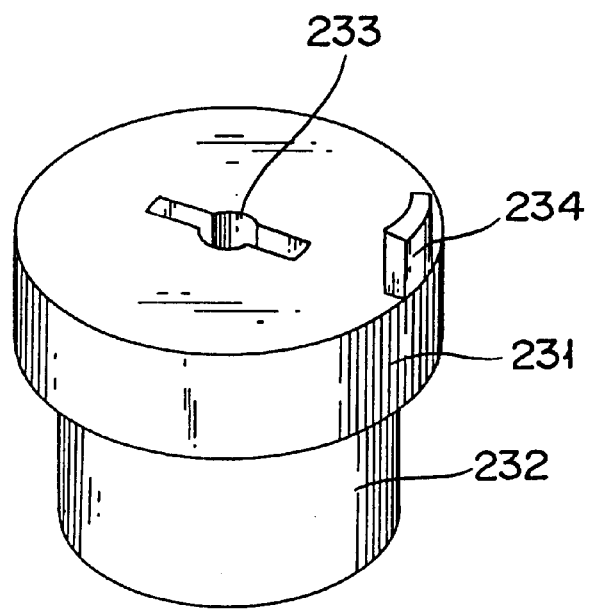
FIG. 14 is a perspective view of the image guide fixing part.

FIG. 13 is a cross section showing the image guide fixing part 230 and the protection tube 400, and FIG. 14 is a perspective view of the image guide fixing part 230.

The image guide fixing part 230 comprises a rotator 231 and a protection tube mounting part 232.

The rotator 231 holds the fiber scope 270 covered by the lead wires 215 and the protective pipe 274. Therefore, the rotator 231 is provided with a through hole 233 through which the protective pipe 274 and the two lead wires 215 pass. As shown in FIG. 14, the hole 233 has a part to which the protective pipe 274 is fitted, and another part into which the lead wires 215 are inserted. The protective pipe 274 is fitted to the hole 233 and fixed with adhesive or other means. The rotator 231 is formed a protruding part 234 as shown in FIG. 14.

The protective tube 400, on the outside of which a ring-like keeper 235 is mounted, is inserted into the protective tube fitting part 232. The keeper 235 is placed between the jointing part 240 and the image guide fixing part 230 as shown in FIG. 9 and affixed to the protective tube 400. The protective tube 400 extends to the display device 300 and allows the fiber scope 270 and the lead wires 215 to pass through it. The protective tube 400 prevents the fiber scope 270 and the lead wires 215 from damage or bending that may cause damage. The fiber scope 270 is protected by the protective tube 400 where it is not protected by the protective pipe 274. Since the protective pipe 274 does not pass through the protective tube 400, the protective tube 400 can flex to a degree that does not cause damages to the fiber scope 270 and the lead wires 215.

Figure 15:
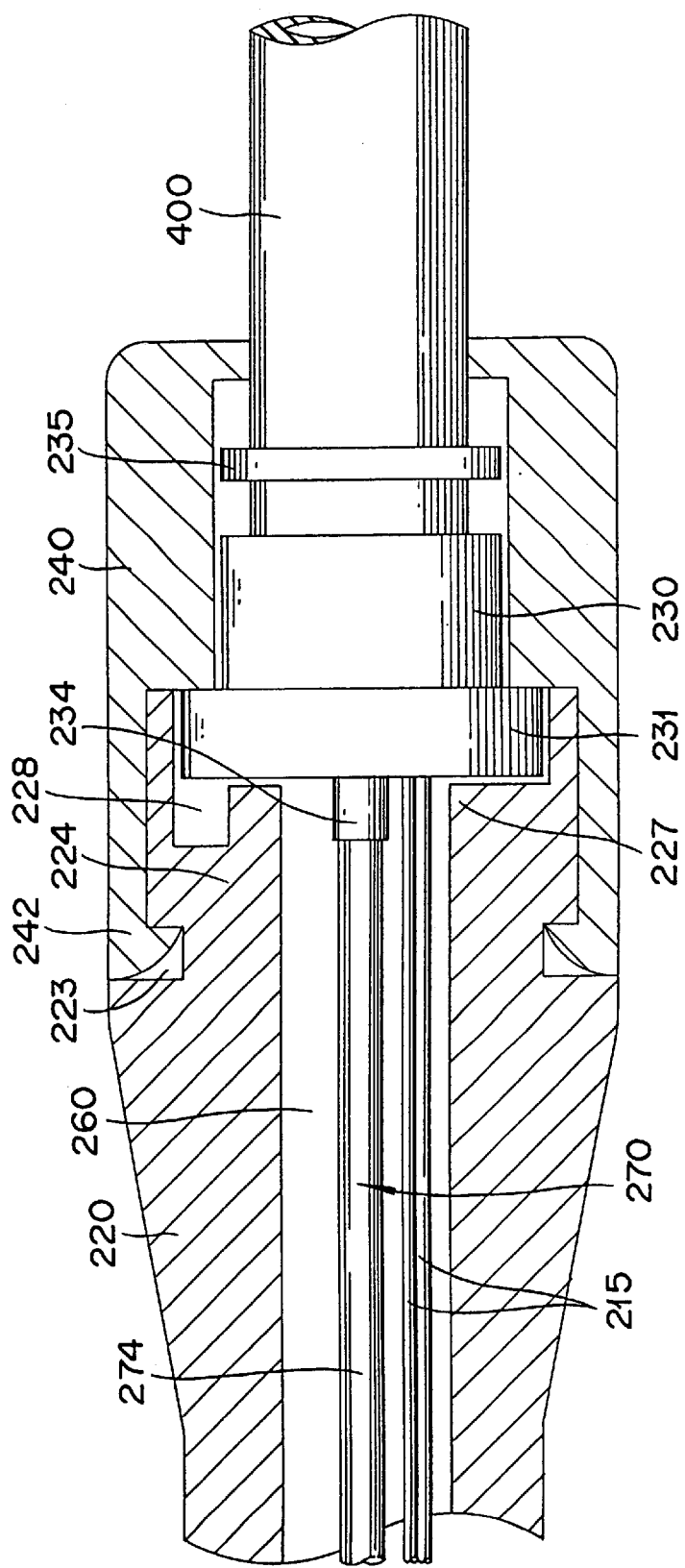
FIG. 15 is a cross section of an assembly of the holding pipe, the image guide fixing part and a joint.

FIG. 15 is a cross section of an assembly of the holding pipe 220, the image guide fixing part 230 and the jointing part 240.

First, the protective tube 400, which carries inside the fiber scope 270 and the lead wires 215, is inserted into the image guide fixing part 230. The fibers scope 270 is inserted into the protective pipe 274, and is inserted with the lead wires 215 into the hole 233 formed in the image guide fixing part 230 (see FIG. 14). The rotator 231 of the image guide fixing part 230 is inserted into the supporting pipe 220 through a small space. The jointing part 240 has a hook 242 to engage with a notch 223 formed on the second end 224 of the supporting pipe 220. The jointing part 240 engaged with the supporting pipe 220 encloses a portion of the protective tube 400 and the image guide fixing part 230. The keeper 235 is fastened on the outer periphery of the protective tube 400 in the inside of the jointing part 240. The keeper 235, as it cannot come out of the jointing part 240, prevents the protective tube 400 from slipping off the jointing part 240.

Thus, the supporting pipe 220 and the jointing part 240 are jointed together into a unitized structure by means of a male-female fit. On the other hand, there is a slight clearance between the supporting pipe 220 and the image guide fixing part 230. Therefore, the supporting pipe 220 and the jointing part 240 are rotatable relative to the image guide fixing part 230. However, the image guide fixing part 230 has the protective pipe 274 affixed to it, and the protective pipe 274 has the non-rotating fiber scope 270 affixed to its inside, the image guide fixing part 230 itself does not rotate. In other words, the supporting pipe 220 and the jointing part 240 are rotatable around the image guide fixing part 230.

The two lead wires 215 protruding the hole 233 of the image guide fixing part 230 are connected to the light source 214 as shown in FIG. 10. Since the light source 214 is located at a fixed position inside the first end part 222 of the supporting pipe 220, it rotates with the supporting pipe 220. Therefore, unless there is a restriction to the rotation of the supporting pipe 220, the lead wires 215 will be twisted between the stationary image guide fixing part 230 and the rotating fit end 222. This will damage the wires 215. In order to prevent the damage of the lead wires 215, a latching mechanism is provided between the image guide 230 and the supporting pipe 220.

This latching mechanism prevents the supporting pipe 220 from rotating more than one revolution by the protruding part 234 interferes with an extending part 227. The protruding part 234 is formed on the image guide fixing part 230. The extending part 227 is formed in such a way that it abuts against the protruding part 234 before the supporting pipe 220 makes one revolution around the image guide fixing part 230. The extending part 227 is formed in a part of a ring-shaped space 228 formed by cutting out the inside of the second end 224.

Next, the constitution of the display device 300 will be described more specifically.

Figure 16:
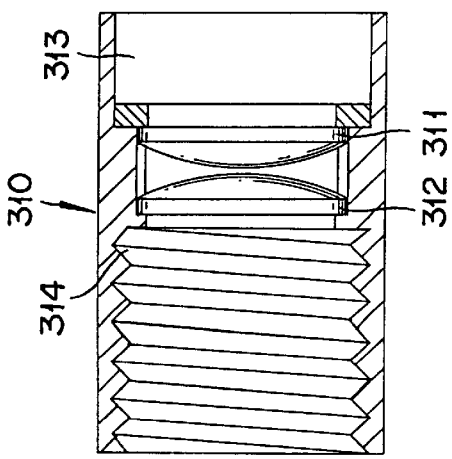
FIG. 16 is a cross section of the display device.
Figure 16:
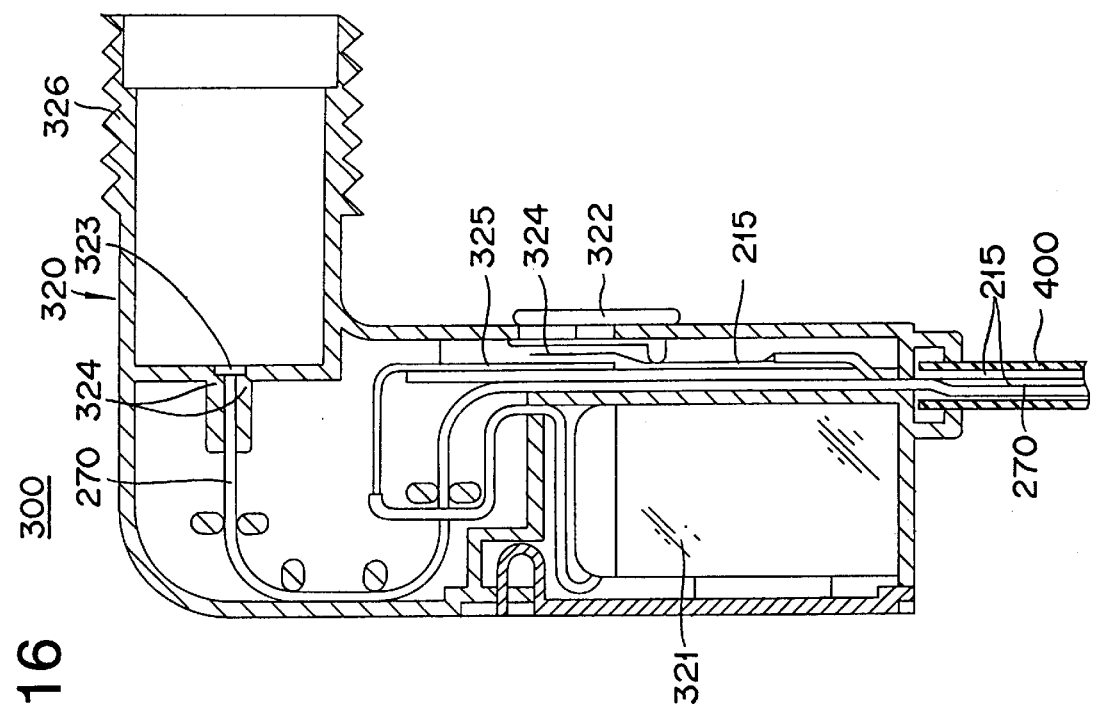

FIG. 16 is a cross section of the display device 300.

The display device 300 comprises a eyepiece part 310 and a display main body 320.

The eyepiece part 310 has a pair of plano-convex lenses 311 and 312. To view an image in the auditory canal, it is viewed from the flat side of the plano-convex lens 311 through a shade 313. The shade 313 is used to generate a darkened area around the plano-convex lens 311 to make it easier to view the images of the inside of the auditory canal formed in the flat convex lens 311. The flat convex lens 312 is placed in such a way that its convex side faces the convex side of the convex face of the flat convex lens 311 across a short distance. In the eyepiece part 310, a threaded hole 314 is formed on the flat face side of the flat convex lens 312.

The display main body 320 comprises a battery 321 for supplying electric power to the light source 214, a switch 322 for connecting said battery 321 and the light source 214, and a convex lens 323 for enlarging the images transmitted through the fiber scope 270. When the user slides (turns on) the switch 322 to make the contact between the lead wires 215 and the lead wires 325 via a metal piece 324, the battery 321 supplies power to the light source 214. The convex lens 323 is placed in the vicinity of the end face of the fiber scope 270 that is threaded through the protective tube 400 from the ear-pick unit 200. The positions of the end face of the fiber scope 270 and the convex lens 323 are defined by a wall 324 formed on the inside of the display main body 320.

The display main body 320 has a threaded part 326, which is threaded into the threaded hole 314.

When the threaded part 326 is threaded into the threaded hole 314, the eyepiece part 310 and the display main body 320 becomes unitized. The distance between the convex lens 323 and the plano-convex lens 312 can be adjusted by means of adjusting the amount of the threading engagement of the threaded part 326. Therefore, when the lens becomes out of focus because the distance between the lenses of the display device 300 changes minutely due to the temperature change or other reasons, it can be easily adjusted by manual adjustment.

Next, the operation of the endoscopic auditory canal cleaning apparatus 100 will be described.

First, the user of the endoscopic auditory canal cleaning apparatus 100 turns on the switch 322 of the display device 300, and inserts the ear-pick main body 212 of the ear-pick unit 200 and the fiber scope 270 into the user's ear.

When the switch 322 is turned on, the battery 321 supplies electric power to the light source 214 through the lead wires 215. The light source 214 illuminates and irradiates the end face 213 of the ear-pick main body 212. The light is transmitted through the ear-pick main body 212 and is irradiated from the irradiation part 219 to illuminate the auditory canal.

When the auditory canal is illuminated, the fiber scope 270 can capture the images inside of the auditory canal. The captured images are transmitted to the display device 300 through the fiber scope 270, and enlarged by the convex lens 323 in the display device 300. The enlarged images are displayed via the plano-convex lens 311 and via the plano-convex lens 312. Since the display device 300 enlarges the images of the inside of the auditory canal, the user can easily clean the auditory canal.

The user can remove earwax viewing the images of the inside of the auditory canal. If the picture is not clear, the user can adjust the lens focus by adjusting the amount of engagement of the threaded part 326 with the threaded hole 314 by turning the eye-piece part 310, thus adjusting the distance between the convex lens 323 and the plano-convex lens 312.

To handle the ear-pick unit 200, the user holds a part of the holding part 250 of the ear-pick unit 200. This holding part 250 is rotatable around the image guide fixing part 230. Since the fiber scope 270 that extends from the image guide fixing part 230 does not rotate, the image captured by the fiber scope 270 stays always in one direction. The ear-picking main body 212 affixed to the ear-pick mounting part 210 is rotatable around the fiber scope 270. Therefore, the user can clean the inside of the auditory canal to rotate the ear-pick main body 212 arbitrarily while viewing the image in one direction, so that it is very convenient.

Moreover, because of the latching mechanism that limits the relative rotation between the image guide fixing part 230 and the holding part 250, the lead wires 215 that connect to the light source 214 of the ear-pick mounting part 210 are prevented from any damages due to over-twisting in the inner space 260 of the holding part 250.

Although a case of using the fiber scope 270 as the image capturing means is described in the third embodiment as above, it is also possible to use an image sensor such as a CCD camera as the image capturing means. In that case, a device for forming images by image processing the signals from the CCD camera will be used instead of convex lenses and plano-convex lenses for enlarging the images in the display device.

Thus, the endoscopic auditory canal cleaning device according to this invention will provide the following benefits.

The light from the light source transmitted through the ear-pick main body illuminates the inside of the auditory canal. The images of the inside of the auditory canal illuminated by the light are captured by the image capturing means and guide to the display means to be displayed. The user can remove foreign objects in the user's own ear while watching the images. Also, since the holding part rotates around the image capturing means, it is possible to clean the inside of the auditory canal by rotating the ear-pick main body together with the holding part while maintaining the images displayed by the display means in a fixed direction.

The ear-pick main body can be removed from the holding part and replaced.

The light from the light source transmitted through the ear-pick main body illuminates the inside of the auditory canal. The images of the inside of the auditory canal illuminated by the light are captured by the image capturing means and guide to the display means to be displayed. The user can remove foreign objects in the user's own ear while watching the images. Also, since the ear-pick main body rotates around the image capturing means, it is possible to clean the inside of the auditory canal by rotating the ear-pick main body alone while maintaining the images displayed by the display means in a fixed direction.

It is possible to remove foreign objects while watching the scraping part.

It is possible to supply the light of the light source to the ear-pick main body without causing any attenuation.

Cleaning of the inside of the auditory canal is made easy because the images of the inside of the auditory canal are displayed in large, visible sizes.

It is possible to prevent the contamination and damage of the distal end of the fiber scope.

Lens replacement can be easily done.

It is possible to view the images of the inside of the auditory canal using an image sensor.

It is possible to guide light from a remote light source into the auditory canal.

Images inside the ear are captured by the object lens at the distal end of the image capturing means and are guided to the display device by means of the fiber scope.

Since the optical fiber is fixed and only the ear-pick main body is held free to rotate, the optical fiber does not get twisted by rotating together with the ear-pick main body.

Since the light is guided to the inside of the auditory canal to illuminate it, it is possible to capture the images inside the auditory canal and watch the images outside of the auditory canal. Therefore, it is possible to clean the auditory canal safely and securely.

Since the ear-pick main body having the earwax removing part is interchangeable, so that it can be replaced if it gets contaminated and can be maintained always hygienic.

Since the ear-pick main body rotates around the image capturing means, it is possible to clean the inside of the auditory canal by rotating the ear-pick main body alone while maintaining the images displayed by the display means.

Since the display means displays the images of the inside of the auditory canal enlarging to sizes easy to watch, cleaning of the inside of the auditory canal can be done easily.

The entire disclosures of Japanese Patent Application Nos. 11-323,590 filed on Nov. 15, 1999 and 2000-217,978 filed on Jul. 18, 2000 including specifications, claims and summaries are incorporated herein by reference in their entireties.

What is claimed is:

1. Endoscopic auditory canal cleaning apparatus comprising:

an ear-pick main body, which is equipped with a scraping part at its distal end and is formed to guide light to said distal end;

a light source, which generates said light;

an image capturing means, which captures images in the inside of the auditory canal;

a display means, which displays the images captured by said image capturing means;

a hollow holding part, which holds said ear-pick main body and said image capturing means, wherein said image capturing means passes through said hollow holding part; and said hollow holding part and said ear-pick main body rotate freely, while maintaining said images displayed by said display means in a fixed direction, about the optical axis of said image capturing means.

2. Endoscopic auditory canal cleaning apparatus of claim 1 wherein said ear-pick main body is freely replaceable from said holding part.

3. Endoscopic auditory canal cleaning apparatus of claim 1 or wherein said scraping part is placed in the field of view of said image capturing means.

4. Endoscopic auditory canal cleaning apparatus of claim 1 or wherein said light source is placed in such a way that radiating light directly irradiates said ear-pick main body.

5. Endoscopic auditory canal cleaning apparatus of claim 1 or wherein said image capturing means is included a fiber scope and said display means displays the images guided through said fiber scope in enlarged scales.

6. Endoscopic auditory canal cleaning apparatus of claim 5 wherein said fiber scope is equipped with a covering member that covers its distal end.

7. Endoscopic auditory canal cleaning apparatus of claim 6 wherein said covering member includes an objective lens.

8. Endoscopic auditory canal cleaning apparatus of claim 1 or wherein said image capturing means includes an image sensor and said display means displays images formed by image processing signals transmitted from said image sensor.

* * * * *